(12) United States Patent
Hugon et al.

(10) Patent No.: US 6,255,054 B1
(45) Date of Patent: Jul. 3, 2001

(54) POLYMORPHISM OF THE HUMAN GLUR-5 GENE AND RISK FACTOR FOR ALZHEIMER DISEASE

(76) Inventors: Jacques Hugon, 17 Avenue Albert Thomas; Marie-Claire Baclet, 26 Rue Saint Eloi, both of 87000 Limoges (FR)

( * ) Notice: Subject to any disclaimer, the term of this patent is extended or adjusted under 35 U.S.C. 154(b) by 0 days.

(21) Appl. No.: 09/392,486

(22) Filed: Sep. 9, 1999

(51) Int. Cl.$^7$ .............................. C12Q 1/68; C07H 21/04
(52) U.S. Cl. ..................... 435/6; 536/23.1; 536/23.5; 536/24.1; 536/24.33; 536/24.31
(58) Field of Search ................ 435/6; 536/23.1, 536/23.5, 24.1, 24.33, 24.31

(56) References Cited

U.S. PATENT DOCUMENTS

| | | | |
|---|---|---|---|
| 5,716,828 | 2/1998 | Roses et al. | 435/6 |
| 5,853,995 | * 12/1999 | Lee | 435/6 |

OTHER PUBLICATIONS

Gregor et al. "Genetic and physical mapping of the GLUR5 glutamate receptor gene on human chromosome 21". Human Genetics, vol. 94, pp. 565–570, 1994.*

Ahren "Biochemical, Reagent Kits offer Scientists good return on investment" www.the–scientist.library.upenn.edu/yr1995/july/tools_950724.html, Dec. 22, 1998.*

Paul Gregor et al., "Genetic and physical mapping of the GLUR5 glutamate receptor gene on human chromonsome 21" *Hum Genet*, Spring 1994, pp. 94:565–570.

Qing Guo et al., "Increased vulnerability of hippocampal neurons to excitotoxic necrosis in presenilin–1 multant knock–in mice", *Nature Medicine*, , Jan. 1999, vol. 5, No. 1, pp. 101–106.

Takashi Hayashi et al., "The AMPA receptor interacts with and signals through the protein tyrosine kinase Lyn", *Nature*, Jan. 1999, vol. 397, pp. 72–76.

Dennis W. Choi, Glutamate Neurotoxicity and Diseases of the Nervous System, *Neuron*, Oct. 1998, vol. 1, pp. 623–634.

Guy McKhann et al., "Clinical Diagnosis of Alzheimer's disease: Report of the NINCDS–ADRDA Work Group under the auspices of Department of Health and Human Services Task Force on Alzheimer's Disease", *Neurology*, Jul. 1984, vol. 34, pp. 939–944.

K.A. Jellinger et al., "Neuropathology of Alzheimer's disease: a critical update", *J Neural Transm*, Spring 1998, [Suppl] pp. 54:77–95.

(List continued on next page.)

*Primary Examiner*—Lisa B. Arthur
*Assistant Examiner*—Jeanine Goldberg
(74) *Attorney, Agent, or Firm*—Mason, Kolehmainen, Rathburn & Wyss

(57) ABSTRACT

The present invention concerns a method and kit for determining if a subject is at increased or decreased risk of developing Alzheimer's disease. The invention further concerns vectors, transformed cells or transgenic mammals which can be used in a method for the screening of compound capable of modulating the expression of the GluR-5 gene or the activity of the GluR-5 receptor. The compounds selected by the method of the invention, as medicament for the treatment or the prevention of Alzheimer's disease, also form part of the present invention.

8 Claims, 1 Drawing Sheet

OTHER PUBLICATIONS

N. Schupf et al., "Earlier onset of Alzheimer's disease in men with Down snydrome", *Neurology*, 1998, pp. 50:991–995.

Thomas Sander et al., "Allelic Association of Juvenile Absence Epilepsy With a GluR5 Kainate Receptor Gene (GRIK1) Polymorphism", *American Journal of Medical Genetics*, 1997, pp. 74:416–421.

J. Timothy Greenamyre et al., "Glutamate Transmission and Toxicity in Alzheimer's Disease", *Prog. Neuro–Psychopharmacol. & Biol. Psychiatry*, 1998, vol. 12, pp. 421–430.

Mark P. Mattson, "Antigenic Changes Similar to Those Seen in Neurofibrillary Tangles Are Elicited by Glutamate and $Ca^{2+}$Influx in Cultured Hippocampal Neurons", *Neuron*, Jan. 1990, vol. 2, pp. 105–117.

Susana E. Montoya et al., "Bleomycin hydrolase is associated with risk of sporadic Alzheimer's disease", *Nature Genetics*, Mar. 1998, vol. 18, pp. 211–212.

Q Hu et al., Abstract of "The human FE65 gene: genomic structure and an intronic biallelic polymorphism associated with sporadic dementia of the Alzheimer type.", *Hum. Genet.*, Sep. 1998, pp. 103(3):295–303.

L. Li et al, Abstract of "Polymorphic tetranucleotide repeat site within the intron 7 of the beta–amyloid precursor protein gene and its lack of association with Alzheimer's disease", *Hum. Genet.*, Jul. 1998, pp. 103(1):86–89.

E.K. Luedecking et al., Abstract of "Genetic polymorphism in the persyn (gammasynuclein) gene and the risk of Alzheimer's disease", *Neurosci Lett*, Feb. 19, 1999, pp. 261(3):186–188.

\* cited by examiner

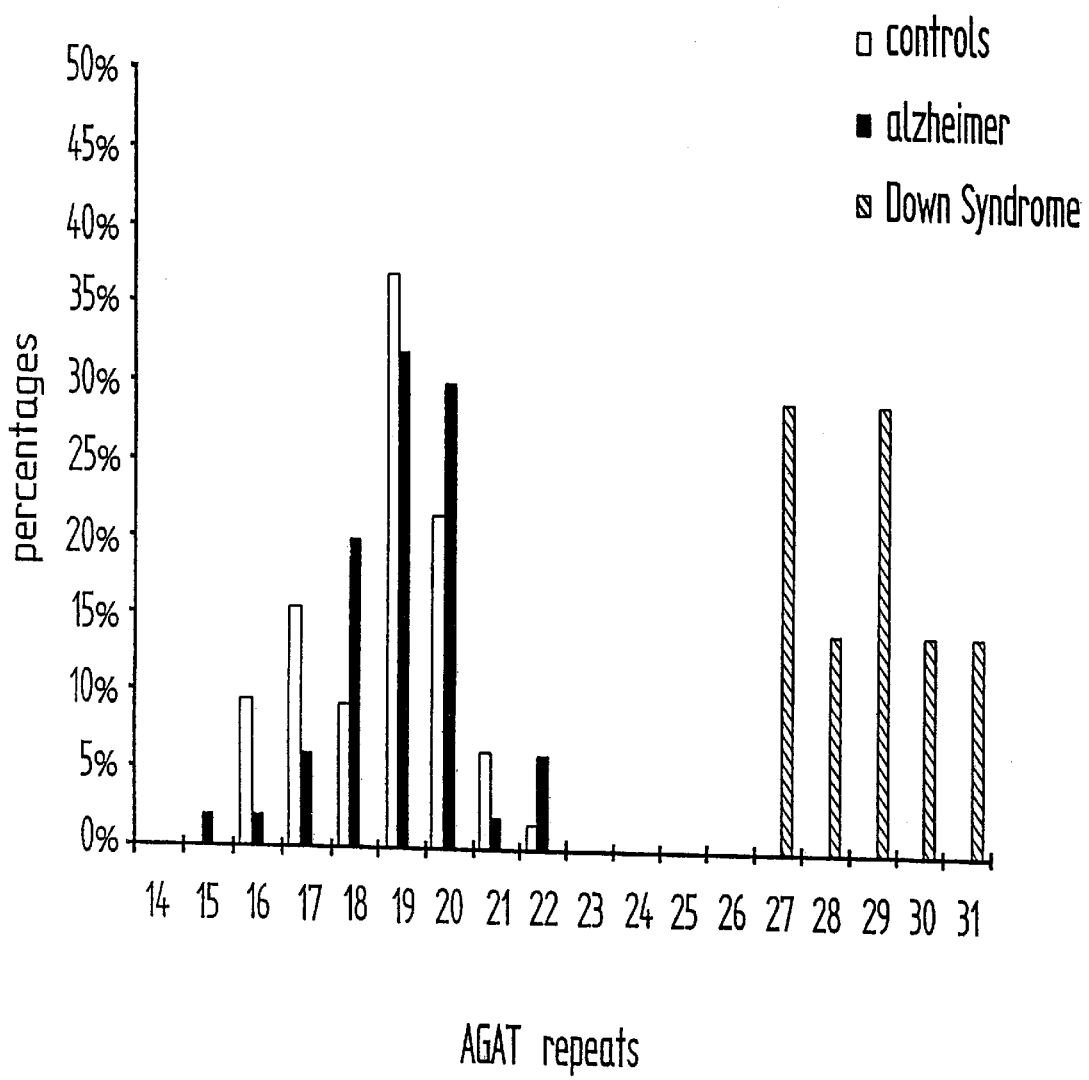

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Primer derived from Human glutamate (Kainate)
      receptor 5 (GluR-5) gene

<400> SEQUENCE: 1
gctaaataga tatatgataa acgg                                              24

<210> SEQ ID NO 2
<211> LENGTH: 23
<212> TYPE: DNA
<213> ORGANISM: Artificial Sequence
<220> FEATURE:
<223> OTHER INFORMATION: Primer derived from Human glutamate (Kainate)
      receptor 5 (GluR-5) gene

<400> SEQUENCE: 2
ctggcagtaa atgtctatga aac                                               23
```

US 6,255,054 B1

POLYMORPHISM OF THE HUMAN GLUR-5 GENE AND RISK FACTOR FOR ALZHEIMER DISEASE

FIELD OF THE INVENTION

The present invention concerns a method and kit for determining if a subject is at increased or decreased risk of developing Alzheimer's disease. The invention further concerns vectors, transformed cells or transgenic mammals which can be used in a method for the screening of compound capable of modulating the expression of the GluR-5 gene or the activity of the GluR-5 receptor. The compounds selected by the method of the invention, as medicament for the treatment or the prevention of Alzheimer's disease, also form part of the present invention.

BACKGROUND OF THE INVENTION

Alzheimer's disease (AD) is marked by the progressive decline of cognitive functions in affected patients and neuropathological features include brain neuronal loss (See Jellinger, & K. A., Bancher, C. J Neural Trans Suppl 54,77–95 (1998)). The causes of sporadic forms of AD representing more than 90% of all cases are unknown. In the brain glutamate receptors mediate fast excitatory neurotransmission and excitotoxicity, a mechanism proposed at the origin of neuronal death in neurodegenerative disorders including AD (See Choi, D. W. Neuron 1,623–634 (1988)).

While there has been considerable research into the mechanisms underlying Alzheimer's disease, it is desirable to develop methods for determining if a subject is at increased risk of developing Alzheimer's disease, using new markers, alone or together with another already known marker or more. It is also desirable to find new ways to investigate and combat this disorder.

For these reasons, the inventors have investigated the polymorphic variations of the human glutamate (kainate) receptor 5 (GluR-5) gene localized on chromosome 21. A variable number of tetraplet repeats AGAT is present in an intronic region of this gene (Ref. GENBANK Accession Number AP000238) and can be assessed by gene sequencing (See Gregor, P. et al. Hum Genet 94, 565–570 (1994)).

The inventors have provided evidence that the total number of tetraplet repeats AGAT present in an intronic region of this gene is significant of the risk of developing Alzheimer's disease.

SUMMARY OF THE INVENTION

The present invention is directed to a method for determining if a subject is at increased or decreased risk of developing Alzheimer's disease, preferably sporadic forms of Alzheimer's disease, comprising the steps of:

a) collecting a biological sample containing genomic DNA from the subject, preferably isolated from venous blood lymphocytes;

b) determining the tetranucleotide AGAT repeats number present in the intronic polynucleotide of the gene GluR-5 which can be amplified by polymerase chain reaction with the primers having the sequences SEQ ID No: 1 and SEQ ID No: 2 on each allele;

c) calculating the total number of tetranucleotide AGAT repeats by adding the tetranucleotide AGAT repeats number determined for each allele in step b);

d) observing whether or not the subject is at increased or decreased risk of developing Alzheimer's disease by observing the total number of tetranucleotide AGAT repeats determined in step c) wherein a total number of AGAT repeats equal or superior to a significant threshold value determined by statistical analysis from a reference population indicates said subject is at increased risk of developing Alzheimer's disease and wherein a total number of AGAT repeats inferior to said significant threshold value indicates said subject is at decreased risk of developing Alzheimer's disease.

In a preferred embodiment, the present invention is directed to a method according to the invention wherein said significant threshold value determined by statistical analysis is 18±1, preferably 18, provided that said subject is known not to be affected by the Down syndrome In a further preferred embodiment, the tetranucleotide AGAT repeats number present in the intronic polynucleotide of the gene GluR-5 on each gene GluR-5 allele of the chromosome 21 is obtained by determining the size of and/or sequencing the amplified products obtained after polymerase chain reaction.

In a second aspect, the present invention relates to a method for determining if a subject is at increased or decreased risk of developing Alzheimer's disease according to the invention, characterized in that said method further comprises a second method for assaying a biological sample from said subject for levels of at least an additional marker associated with the increased risk of developing Alzheimer's disease, the presence of a significant level of said at least one marker allowing to confirm if said subject is at increased risk of developing Alzheimer's disease.

In a particularly preferred embodiment, said second method comprises the following steps of:

(i) detecting the presence or absence of an ApoE4 isoform in a biological sample of said subject by using at least one reagent that specifically detects apolipoprotein E type 4 (ApoE4), wherein said reagent is selected from the group consisting of antibodies that selectively bind ApoE4, and oligonucleotide probes that selectively bind to DNA encoding ApoE4; and (ii) observing if the presence of ApoE4 is or is not detected with said at least one reagent wherein the presence of ApoE4 confirms said subject is at increased risk of developing Alzheimer's disease.

Said at least additional marker associated in conjunction with the method of the present invention can be also selected from the group of markers consisting of bleomycin hydrolase gene polymorphism, FE65 protein gene polymorphism, polymorphic tetranucleotide ATTT repeat site within the intron 7 of the beta-amyloïd precursor protein gene and the persyn (gamma-synuclein) gene polymorphism.

In a third aspect the present invention concerns cloning and/or expression vector comprising a nucleic acid sequence containing between 7 and 14 tetranucleotide AGAT repeats in the intronic polynucleotide of the gene GluR-5 obtainable from biological sample of a subject at decreased or increased risk of developing Alzheimer's disease by polymerase chain reaction with the primers having the sequences SEQ ID No: 1 and SEQ ID No: 2.

Host cell transformed by said vector or mammal, except man, comprising said transformed cell also form part of the present invention.

In a further aspect the present invention is directed to a method for screening or selecting chemical or biochemical compound capable of modulating the expression or the activity of GluR-5 gene characterized in that it uses a vector, a cell or a mammal according to the invention.

In a further aspect the method of the present invention could be used to select patient who may be treated with compound capable of modulating the expression of the GluR-5 gene or the activity of the GluR-5 receptor, according to a pharmacogenomic selection.

In a further aspect the present invention concerns a kit for determining if a subject is at increased or decreased risk of developing Alzheimer's disease comprising at least one pair of primers capable of amplifying the tetranucleotide AGAT repeats number present in the intronic polynucleotide of the gene GluR-5 which can be amplified by polymerase chain reaction with the primers having the sequences SEQ ID No: 1 and SEQ ID No: 2.

In a preferred embodiment the kit of the present invention comprises in addition instructions for determining that the subject is at increased or decreased risk of developing Alzheimer's disease by:

(i) calculating the total number of tetranucleotide AGAT repeats by adding the tetranucleotide AGAT repeats number determined for each allele with said at least one pair of primers; and (ii) determining whether or not the subject is at increased or decreased risk of developing Alzheimer's disease by observing if the total number of AGAT repeats is equal or superior to a significant threshold value determined by statistical analysis from a reference population, preferably 18±1, wherein a total number of AGAT repeats equal or superior to said significant threshold value indicates said subject is at increased risk of developing Alzheimer's disease and wherein a total number of AGAT repeats inferior to said significant threshold value indicates said subject is at decreased risk of developing Alzheimer's disease.

The kit of the present invention further comprising means for assaying a biological sample from said subject for levels of at least an additional marker associated with the increased risk of developing Alzheimer's disease, preferably the ApoE4 marker, also forms part of the present invention.

In another aspect the present invention comprises kit for screening an agent capable of modulating the expression of the GluR-5 gene or the activity of the GluR-5 receptor comprising a vector, a cell or a mammal according to the invention.

Chemical or biochemical compounds capable of modulating the expression of GluR-5 gene or the activity of the GluR-5 receptor, characterized in that they are selected by a method for screening of the invention, particularly for the prevention or treatment of Alzheimer's disease, are another object of the present invention.

BRIEF DESCRIPTION OF THE DRAWING

The accompanying single Figure shows a distribution of AGAT repeats in Alzheimer, control and Down syndrome populations. Percentages of Alzheimer patients, controls and Down syndrome individuals versus AGAT repeats.

DETAILED DESCRIPTION OF THE INVENTION

The present invention relates to a method for determining if a subject is at increased or decreased risk of developing Alzheimer's disease comprising the steps of:

a) collecting a biological sample containing genomic DNA from the subject;

b) determining the tetranucleotide AGAT repeats number present in the intronic polynucleotide of the gene GluR-5 which can be amplified by polymerase chain reaction with the primers having the sequences SEQ ID No: 1 and SEQ ID No: 2on each allele;

c) calculating the total number of tetranucleotide AGAT repeats by adding the tetranucleotide AGAT repeats number determined for each allele in step b);

d) observing whether or not the subject is at increased or decreased risk of developing Alzheimer's disease by observing the total number of tetranucleotide AGAT repeats determined in step c) wherein a total number of AGAT repeats equal or superior to a significant threshold value determined by statistical analysis from a reference population, indicates said subject is at increased risk of developing Alzheimer's disease and wherein a total number of AGAT repeats inferior to said significant threshold value indicates said subject is at decreased risk of developing Alzheimer's disease.

The inventors have indeed demonstrate that the addition of the number of tetranucleotide AGAT repeats present on each gene GluR-5 allele of the chromosome 21 (named "total number" in the present invention) is significant of the risk of developing Alzheimer's disease (see the drawing figure).

Said intronic polynucleotide of the gene GluR-5 which can be amplified by polymerase chain reaction with the primers having the sequences SEQ ID No: 1 and SEQ ID No: 2, and which contains the tetranucleotide AGAT repeats corresponds to the fragment nt 5672–5789 of the GRI K1 sequence (GENBANK Accession Number AP000238).

Generally, when the subject to be tested presents two copies of the chromosome 21 (known not to be affected by the Down syndrome), steps b) and c) of the present method are the following:

b) determining the tetranucleotide AGAT repeats number present in the intronic polynucleotide of the gene GluR-5 which can be amplified by polymerase chain reaction with the primers having the sequences SEQ ID No: 1 and SEQ ID No: 2, on each different allele if the subject exhibits a heterozygosity on this locus, or on the only allelic form if the subject exhibits a homozygosity on this locus;

c) calculating the total number of tetranucleotide AGAT repeats by adding the tetranucleotide AGAT repeats number determined for each different allele in step b) (heterozygous subject) or doubling the tetranucleotide AGAT repeats number determined for the only allelic form in step b) (homozygous subject).

In particular, the inventors have shown that a total number of AGAT repeats equal or superior to 18 indicates the tested subject is at increased risk of developing Alzheimer's disease, preferably sporadic forms of Alzheimer's disease, provided that said subject is known not to be affected by the Down syndrome.

The significant threshold value of 18 has been determined from the reference population selected in the examples and used for the statistical analysis. This average threshold value may be slightly different (preferably 18±1) depending on the size of the selected reference population used for its calculation.

In a preferred embodiment, the present invention relates to a method according to the invention, wherein a total number of AGAT repeats superior to 20, preferably 21 indicates that said subject is at very high risk of developing Alzheimer's disease, provided that said subject is known not to be affected by the Down syndrome.

In the particular case wherein the subject is affected by the Down syndrome and presents three copies of the chromosome 21, the present invention relates to a method for determining if a subject is at increased or decreased risk of developing Alzheimer dementia syndrome related to Down syndrome comprising the steps of:

a) collecting a biological sample containing genomic DNA from the subject;

b) determining the tetranucleotide AGAT repeats number present in the intronic polynucleotide of the gene GluR-5 which can be amplified by polymerase chain reaction with the primers having the sequences SEQ ID No: 1 and SEQ ID No: 2, on the three alleles;

c) calculating the total number of tetranucleotide AGAT repeats by adding the tetranucleotide AGAT repeats number determined for each of the three alleles in step b);

d) observing whether or not the subject is at increased or decreased risk of developing Alzheimer dementia syndrome related to Down syndrome by observing the total number of tetranucleotide AGAT repeats determined in step c) wherein the risk of developing Alzheimer dementia syndrome related to Down syndrome is all the more increased since the total number of AGAT repeats is large and wherein the risk of developing Alzheimer dementia syndrome related to Down syndrome is all the more decreased since the total number of AGAT repeats is small.

According to the small number of patients affected by the Down syndrome tested in the example, the significant threshold value of the total number of tetranucleotide AGAT repeats from which said risk is increased has not been calculated. By selecting a reference population representative of these subjects, this threshold value may be calculated by a skilled man in a same manner as calculated for subjects which are not affected by the Down syndrome.

According to the present invention, any biological sample which contains the genomic DNA of the tested subject may be employed in step a) of the present method, including tissue samples and blood samples, white blood cells being particularly convenient source, preferably venous blood lymphocytes.

The step b) of determining on each gene GluR-5 allele of the chromosome 21 the tetranucleotide AGAT repeats number present in the intronic polynucleotide of the gene GluR-5 which can be amplified by polymerase chain reaction with the primers having the sequences SEQ ID No: 1 and SEQ ID No: 2may be carried out either directly or indirectly by any suitable means.

A variety of techniques are known to those skilled in the art. All generally involve the step of amplification reaction such as a polymerase chain reaction or ligase chain reaction. Amplification of a selected, or target, nucleic acid sequence may be carried out by any suitable means. See generally D. Kwoh and T. Kwoh, Am. Biotechnol. Lab. 8, 14–25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392–396 (1992); G. Walker et al., Nucleic Acids Res. 20, 1691–1696 (1992); R. Weiss, Science 254, 1292 (1991)), transcription-based amplification (see D. Kwoh et al., Proc. Natl. Acad. Sci. USA 86, 1173–1177 (1989)), self-sustained sequence replication (or 3SR) (see J. Guatelli et al., Proc. Natl. Acad. Sci. USA 87, 1874–1878 (1990)), the Q.beta. replicase system (see P. Lizardi et al., BioTechnology 6, 1197–1202 (1988)), nucleic acid sequence-based amplification (or NASBA) (see R. Lewis, Genetic Engineering News 12 (9), 1 (1992)), the repair chain reaction (or RCK) (see R. Lewis, supra), and boomerang DNA amplification (or BDA) (see R. Lewis, supra). Polymerase chain reaction is currently preferred.

In general, DNA amplification techniques involve the use of a pair of probes or primers which specifically bind to the DNA fragment of interest containing the tetranucleotide AGAT repeats present in the gene GluR-5.

In the present method, all the pairs of primers or probes which may be deduced from the nucleotide sequence containing the tetranucleotide AGAT repeats present in the intronic polynucleotide of the gene GluR-5 which can be amplified by polymerase chain reaction with the pair of primers having the sequences SEQ ID No: 1 and SEQ ID No: 2, and which may make it possible to amplify the same nucleotide sequence, in particular the specific fragment of the gene GluR-5 containing the AGAT repeats, can be used.

A PCR protocol for determining the tetranucleotide AGAT repeats number present in each allele of the gene GluR-5 is described in the example of the present specification, with an example of a pair of primers effective for amplification.

In a preferred embodiment, the invention is directed to a method according to the present invention, characterized in that step b) comprises a step of amplification wherein said intronic polynucleotide of the gene GluR-5 containing the tetranucleotide AGAT repeats is specifically amplified by an amplification reaction, preferably by polymerase chain reaction, with the known primers having the sequences SEQ ID No: 1 and SEQ ID No: 2. See, for example, Gregor et al., 1994, incorporated by reference herein.

After the step of amplification, a step of determining precisely the size or the amplified products obtained can be carried out in order to determine the number of the AGAT repeats present in the nucleic acid gene GluR-5 fragment of interest. This step further allows to determine if the subject is homozygous or heterozygous for said nucleic fragment of interest by observing the peak(s) intensity and/or number obtained after PCR amplification.

Said size can be precisely determined by a variety of techniques known to those skilled in the art, for example by capillary electrophoresis technique using the ABI PRISM 310 Genetic Analyser (PE Applied Biosystem).

To better correlate the amplified products sizes and AGAT repeats number, amplified products can be sequenced, after purification, by techniques known to those skilled in the art, for example with the Big dye terminator cycle sequencing kit (PE Applied Biosystems) using the ABI PRISM 310 Genetic Analyser.

Thus, in a more preferred embodiment, the present invention concerns a method according to the invention, wherein the tetranucleotide AGAT repeats number present in the intronic polynucleotide of the gene GluR-5 on each gene GluR-5 allele of the chromosome 21 is obtained in step b) by determining the size of and/or sequencing the amplified products obtained after the step of amplification.

It is preferred and contemplated that the methods of the present invention described herein be used in conjunction with other clinical diagnostic information known or described in the art which are used in evaluation of subjects with Alzheimer's disease or suspected to be at risk for developing such disease.

Therefore, in another aspect, the present invention relates to a method according to the present invention, characterized in that said method further comprises a second method for assaying a biological sample from said subject for levels of at least an additional marker associated with the increased risk of developing Alzheimer's disease, the presence of a significantly level of said at least one marker allowing to confirm if said subject is at increased risk of developing Alzheimer's disease.

Among known marker which are used in evaluation of subjects with Alzheimer's disease or suspected to be at risk for developing such disease, the marker ApoE4 is the preferred additional marker which can be used in conjunction with "the number of AGAT repeats in the gene GluR-5 fragment of interest" marker used in the method of the present invention (see U.S. Pat. No. 5,716,828 incorporated herein by reference for the description of methods which can be used for determining the presence or absence of the ApoE4 isoform in a biological sample).

Thus the present invention is particularly directed to a method of the present invention characterized in that said second method comprises the following steps of:

(i) detecting the presence or absence of an ApoE4 isoform in a biological sample of said subject by using at least one reagent that specifically detects apolipoprotein E type 4 (ApoE4), wherein said reagent is selected from the group consisting of antibodies that selectively bind ApoE4, and oligonucleotide probes that selectively bind to DNA encoding ApoE4; and (ii) observing if the presence of ApoE4 is or is not detected with said at least one reagent wherein the presence of ApoE4 confirms said subject is at increased risk of developing Alzheimer's disease.

Among the other markers known to be correlate to the risk of developing Alzheimer's disease, the preferred markers are those which are selected from the group consisting of the following markers:

bleomycin hydrolase gene polymorphism (Montoya et al., 1998, Nature Genetics, 18, 211–212, incorporated herein by reference);

FE65 protein gene polymorphism (Hu et al., 1998, Hum. Genet., 103, 3, 295–303, incorporated herein by reference);

polymorphic tetranucleotide ATTT repeat site within the intron 7 of the beta-amyloïd precursor protein gene (Li et al., 1998, Hum. Genet., 103, 1, 86–89, incorporated herein by reference); and the persyn (gamma-synuclein) gene polymorphism (Luedecking et al., 1999, Neurosci. Lett., 261, 3, 186–188, incorporated herein by reference).

Thus, the present invention further comprises a method according to the present invention characterized in that said at least additional marker associated is selected from the group of markers consisting of bleomycin hydrolase gene polymorphism, FE65 protein gene polymorphism, polymorphic tetranucleotide ATTT repeat site within the intron 7 of the beta-amyloïd precursor protein gene and the persyn (gamma-synuclein) gene polymorphism.

In another aspect, the present invention comprises cloning and/or expression vector comprising a nucleic acid sequence containing the tetranucleotide AGAT repeats present in the intronic polynucleotide of the gene GluR-5 obtainable from biological sample of a subject at decreased or increased risk of developing Alzheimer's disease by polymerase chain reaction with the primers having the sequences SEQ ID No: 1 and SEQ ID No: 2.

In a preferred embodiment, the invention relates to a cloning and/or expression vector according to the invention wherein said nucleic acid sequence contains more than 5 tetranucleotide AGAT repeats, preferably between 6 to 14 tetranucleotide AGAT repeats, more than 9, 11, or 12 tetranucleotide AGAT repeats are particularly preferred.

Said nucleic acid sequence containing more than 5 tetranucleotide AGAT repeats present in the gene GluR-5 fragment of interest may be obtained after amplification and purification from genomic DNA of biological sample of a subject at decreased or increased risk of developing Alzheimer's disease, or by synthesis.

Such vectors will be prepared according to the methods commonly used by persons skilled in the art, and the clones resulting therefrom may be introduced into an appropriate host by standard methods such as, for example, lipofection, electroporation, calcium phosphate precipitation or heat shock.

The invention comprises, in addition, the host cells, in particular eukaryotic cells, preferably host cells expressing the GluR-5 gene, transformed by the vectors according to the invention. In a preferred embodiment the host cells are neuronal tissue cells expressing the GluR-5 gene or embryonic stem cells.

The invention further concerns the mammals, except man, comprising one of said transformed cells according to the invention.

Among the mammals according to the invention, there will be preferred transgenic animals such as mice, rats or rabbits, exhibiting the GluR-5 gene wherein the nucleic acid sequence of interest containing the AGAT repeats comprises more than 5 tetranucleotide repeats, preferably between 6 to 14 tetranucleotide AGAT repeats. More than 9, 11, or 12 tetranucleotide AGAT repeats are particularly preferred.

They are obtained by homologous recombination on embryonic stem cells, transfer of these stem cells to embryos, selection of the chimeras affected at the level of the reproductive lines, and growth of the said chimeras.

Transgenic mice overexpressing the GluR-5 gene wherein the nucleic acid sequence of interest containing the AGAT repeats comprises more than 5 tetranucleotide AGAT repeats, preferably between 6 to 14 tetranucleotide AGAT repeats are preferred, more than 9, 11, or 12 tetranucleotide AGAT repeats are particularly preferred. The mice could be obtained by transfection of multiple copies of said GluR-5 gene under the control of a strong promoter of an ubiquitous nature, or selective for a type of tissue, preferably the neuronal tissue.

The invention also relates to the use of vector, cells or a mammal according to the invention, for studying the expression and the activity of the GluR-5 receptor, and the direct or indirect interactions between said receptor and the chemical or biochemical compounds which may be involved in the activity of said receptor.

The invention also relates to the use of vector, cells or a mammal according to the invention for the screening of a chemical or biochemical compound capable of interacting directly or indirectly with the GluR-5 receptor, and/or capable of modulating the expression of GluR-5 gene or the activity of GluR-5 receptor.

Also included in the invention are the methods for selecting a chemical or biochemical compound capable of interacting, directly or indirectly, with the receptor GluR-5, and/or allowing the expression of GluR-5 gene or the activity of GluR-5 receptor to be modulated, characterized in that they use a vector, a cell or a mammal according to the invention.

The transformed cells or mammals as described above can also be used as models so as to study the interactions between the GluR-5 receptor and their partners, chemical or protein compounds, which are involved directly or indirectly in the activities of said receptor, and in order to study the different mechanisms of its activity.

In particular, they may be used for the selection of compounds which interact with the GluR-5 receptor or with its polymorphic intronic gene fragment of interest containing the AGAT repeats, as cofactor or as inhibitor, in particular a competitive inhibitor, or alternatively having an agonist or antagonist activity on the physiological roles of the GluR-5 receptor (see the document Gregor et al., 1994 and its references, incorporated herein by reference for a review of the physiological roles of the GluR-5 receptor).

Preferably, said transformed cells or mammal according to the invention will be used as a model allowing, in particular, the selection of products which make it possible to combat the pathologies induced by Alzheimer's disease.

In a further aspect, the invention comprises the determination of the total tetranucleotide AGAT repeats present in said intronic polynucleotide of the gene GluR-5 of a patient as a marker for a pharmacogenomic selection of patients.

The method of the present invention which allows to determine if a subject is at increased or decreased risk of developing Alzheimer's disease could be used to select patients whose response to a drug is linked to the total tetranucleotide AGAT repeats present in the intronic polynucleotide of the gene GluR-5 according to a pharmacogenomic selection, particularly to select patients who may be treated with compound capable of modulating the expression of the GluR-5 gene or the activity of the GluR-5 receptor.

In another aspect, the invention relates to a kit for determining if a subject is at increased or decreased risk of developing Alzheimer's disease comprising at least one pair of primers capable of amplifying the tetranucleotide AGAT repeats number present in the intronic polynucleotide of the gene GluR-5 which can be amplified by polymerase chain reaction with the following primers having the sequences SEQ ID No: 1 and SEQ ID No: 2.

Preferably, the kit according to the present invention is characterized in that said pair of primers is the pair of primers having the sequences SEQ ID No: 1 and SEQ ID No: 2

In a preferred embodiment the kit according to the invention is characterized in that it further comprises instructions, preferably in the same container, for determining that the subject is at increased or decreased risk of developing Alzheimer's disease by:
  (i) calculating the total number of tetranucleotide AGAT repeats by adding the tetranucleotide AGAT repeats number determined for each allele with said at least one pair of primers; and
  (ii) determining whether or not the subject is at increased or decreased risk of developing Alzheimer's disease by observing if the total number of AGAT repeats is equal or superior to a significant threshold value determined by statistical analysis from a reference population, preferably 18±1, wherein a total number of AGAT repeats equal or superior to said significant threshold value indicates said subject is at increased risk of developing Alzheimer's disease and wherein a total number of AGAT repeats inferior to said significant threshold value indicates said subject is at decreased risk of developing Alzheimer's disease.

In a more preferred embodiment, the invention relates to a kit of the invention characterized in that said significant threshold value is 18.

In a more preferred embodiment, the invention relates to a kit of the invention characterized in that the increase or decreased risk of developing Alzheimer's disease to be determined concerns a sporadic Alzheimer's disease.

The present invention further relates to a kit according to the invention characterized in that said kit comprises in addition means for assaying a biological sample from said subject for levels of at least an additional marker associated with the increased risk of developing Alzheimer's disease.

Preferably said at least additional marker associated is selected from the group of markers consisting of apolipoprotein E type 4 (apoE4), bleomycin hydrolase gene polymorphism, FE65 protein gene polymorphism, polymorphic tetranucleotide ATTT repeat site within the intron 7 of the beta-amyloïd precursor protein gene and the persyn (gamma-synuclein) gene polymorphism.

More preferred is a kit characterized in that said at least additional marker associated is apolipoprotein E type 4 (apoE4) and said means comprises at least one reagent that specifically detects apolipoprotein E type 4 (ApoE4), wherein said reagent is selected from the group consisting of antibodies that selectively bind ApoE4, and oligonucleotide probes that selectively bind to DNA encoding ApoE4.

Also forms part of the present invention a kit for screening a modulator agent capable of modulating the expression of GluR-5 gene or the activity of GluR-5 receptor comprising a vector, a transformed cell or a mammal containing said a transformed cell according to the invention.

The chemical or biochemical compounds, characterized in that they make it possible to modulate the expression of GluR-5 gene or the activity of GluR-5 receptor, selected by the method for the screening and/or the selection of compound according to the invention, as defined above, also form part of the invention.

The invention finally relates to the compounds according to the invention as a medicament for the prevention or treatment of Alzheimer's disease or Alzheimer dementia syndrome related to Down syndrome.

A pharmaceutical composition comprising a compound selected by the method for the screening and/or the selection according to the invention is also an object of the present invention.

Preferably, these compounds will be administered by the systemic route, in particular by the intravenous route, by the intramuscular or intradermal route or by the oral route.

Their modes of administration, optimum dosages and galenic forms can be determined according to the criteria generally taken into account in establishing a treatment suited to a patient, such as for example the age or body weight of the patient, the seriousness of his general condition, the tolerance to treatment and the side effects observed, and the like.

Other characteristics and advantages of the invention appear in the remainder of the description with the following examples.

EXAMPLES

Example 1

Selection of patients

50 Patients with sporadic AD were selected fulfilling the NINCDS-ADRDA diagnostic criteria (See McKhann, G. et al. Neurology 34, 939–944 (1984)). 65 Age-matched control patients were included after hospitalization. They were admitted for various diseases including infections and cardiac disorders but without neuropsychiatric disorders. All patients admitted for head traumatisms at the University Hospital for a period of one year were also anonymously enrolled in the study as control population. 7 Individuals with Down syndrome (3 chromosomes 21) were also enrolled. The study design was accepted by the regional ethic committee of Limousin (CCPPRB).

Example 2
GluR-5 Genotyping

Genomic DNA was isolated from venous blood lymphocytes according to the "salting out" method described by Miller et al. (Miller et al., 1988). The region containing the tetranucleotide repeats was amplified by polymerase chain reaction. The primers employed were the primers having the sequences SEQ ID No: 1 and SEQ ID No: 2 (Gregor et al., 1994). The last one was 5' end labeled with 6-FAM fluorescent dye (Perkin Elmer Applied Biosystem). PCR reactions contained 100 ng genomic DNA and 10 pmol of each primer diluted in 25$\mu$l of PCR Supermix reaction mixture (Gibco BRL).

PCR was carried out in a Perkin Elmer 2400 GeneAmp PCR system. Cycling conditions were initial denaturation at 94° C. for 5 min, followed by 25 cycles of denaturation at 94° C. for 30 sec, annealing at 55° C. for 30 sec, synthesis at 72° C. for 30 sec and a final elongation at 72° C. for min. The PCR products (0.1 $\mu$l) were diluted in 25 $\mu$l deionized formamide containing 4 $\mu$mol of GENESCAN-350 Rox size standard (PE Applied Biosystem). Amplified products sizes were determined by capillary electrophoresis using the ABI PRISM 310 Genetic Analyser (PE Applied Biosystem).

To correlate PCR products sizes and AGAT repeats number, homozygous PCR products were purified with the "concert nucleic acid purification system" (GIBCO BRL) and sequenced with the Big dye terminator cycle sequencing kit (PE Applied Biosystems) using the ABI PRISM 310 Genetic Analyser. Results are given in tetranucleotide repeats number.

Example 3
Distribution of AGAT Repeats in Alzheimer, Control and Down Syndrome Populations For each Alzheimer patient, age-matched control and Down syndrome individual, the sum of AGAT repeats of the two GluR-5 alleles (or of the three GluR-5 alleles for Down syndrome individuals) were used for statistical analysis (see FIG. 1 and table 1 below).

tion of unknown origin against the occurrence of AD. This is a partial influence since a few patients were found to have from 14 to 17 AGAT tetraplets. It is well admitted that the risk factor for developing AD pathology is greatly augmented in patients with Down syndrome (See Schupf, N. et al. Neurology 50, 991–995 (1998)) and the large number of AGAT repeats could contribute to this enhanced risk factor. Relations between glutamate transmission, excitotoxicity and the pathophysiology of AD were proposed several years ago based on experimental and clinical data (See Greenamvre. J. T. et al. Proz NeuropsychoPharmacol Biol Psychiatry 12,421–430 (1988)) but no direct evidence involving patients has been produced to date. Glutamate toxicity is able to recapitulate in vitro some of the protein modifications detected in AD (See Mattson, M. P. Neuron 2,105–107 (1990)). Transgenic mice expressing a mutated presenilin 1 comparable to a mutation found in familial AD were described to be more sensitive to kainate toxicity (See Guo, Q. et al. Nat Med. 5,101–106 (1999)). Previously GluR-5 gene polymorphism was positively linked to Juvenile Epilepsy with Absences (See Sander, T. et al. Am J Med. Genet 74,416–421 (1997)). This polymorphism in a subgroup of neurons with kainate receptors could enhance deleterious reactions after ligand-receptor interactions. At the opposite glutamate may exert a trophic neuronal function depending upon different factors (See Hayashi, T. Nature 397,72–76 (1999)). It is tenable to propose that the variation of AGAT tetraplets may modify the trophic action of glutamate but it seems more probable that the resulting effect is an augmented sensitivity to glutamate toxicity although another gain or lack of function cannot be excluded.

The risk factor for AD appears to be lower in nearly 25% of the population having less than 18 AGAT repeats in the two GluR-5 genes. This finding may be used for new diagnostic approaches and drugs modifying glutamate neurotransmission could be administered to patients with AD or Down syndrome.

Obviously, many modifications and variations of the present invention are possible in light of the above teach-

TABLE 1

| | | | Results of statistical analysis. | | | | |
|---|---|---|---|---|---|---|---|
| Patients | N | mean age | AGAT 1 | AGAT 2 | $\chi^2$ | Fisher | odds ratio |
| Controls | 65 | 79.1 | 16 | 49 | $p < 0.04$ | $p < 0.04$ | 2.94 |
| Alzheimer | 50 | 78.9 | 5 | 45 | | | CI 95%: |
| Down syndrome | 7 | 11.8 | 0 | 7 | | | 1.02–9.53 |

Legend of table 1: N is the total number of patients, AGAT 1 represents the number of repeats inferior to 18, AGAT 2 represents the number of repeats equal or superior to 18. CI 95% is the 95% confidence intervals of the odds ratio.

The number of AGAT tetraplets per allele ranges from 7 to 14 for this statistical analysis. An allele exhibiting 6 AGAT tetraplet has been also found in a tested patient ever since. Thus the theoretical number on two chromosomes 21 can range from 12 to 28 and this evaluation was used for statistical analysis (FIG. 1). A significant difference has been found between patients and controls. Only 5 AD patients out of 50 (10%) and 16 out of 65 (24.6%) age-matched control subjects were found to have from 14 to 17 tetraplet repetitions (Chi square: p<.04; Odds Ratio: 2.98; C.I. 95%: 1.02–9.53). All subjects with Down syndrome had between 27 and 31 AGAT repeats in the 3 copies of chromosome 21.

These findings argue that a limited number of combined AGAT repeats in GluR-5 genes is associated with a protecings. Thus, it is to be understood that, within the scope of the appended claims, the invention may be practiced otherwise than as specifically described above.

What is claimed is:

1. A method for determining if a subject is at increased or decreased risk of developing a sporadic form of Alzheimer's disease comprising the steps of:
   a) collecting a biological sample containing genomic DNA from the subject;
   b) determining the tetranucleotide AGAT repeats number present in an intronic polynucleotide of the gene GluR-5 which is amplified by polymerase chain reaction with the primers having the sequences SEQ ID No: 1 and SEQ ID No: 2, on each allele;
   c) calculating the total number of tetranucleotide AGAT repeats by adding the tetranucleotide AGAT repeats number determined for each allele in step b);
   d) observing whether or not the subject is at increased or decreased risk of developing Alzheimer's disease by observing the total number of tetranucleotide AGAT repeats determined in step c) wherein a total number of AGAT repeats equal or superior to 18 indicates said subject is at increased risk of developing said sporadic form of Alzheimer's disease and wherein a total number of AGAT repeats inferior to 18 indicates said subject is at decreased risk of developing said sporadic form of Alzheimer's disease, in the case said subject is known not to be affected by the Down syndrome.

2. A method according to claim 1, wherein the genomic DNA of step a) is isolated from venous blood lymphocytes.

3. A method according to claim 1, characterized in that step b) comprises the amplification of the intronic polynucleotide of the gene GluR-5 which can be amplified by polymerase chain reaction with the primers having the sequences SEQ ID No: 1 and SEQ ID No: 2.

4. A method according to claim 1, characterized in that step b) comprises a step of amplification wherein said intronic polynucleotide of the gene GluR-5 containing the tetranucleotide AGAT repeats is specifically amplified by polymerase chain reaction with the primers having the sequences SEQ ID No: 1 and SEQ ID No: 2.

5. A method according to claim 1, wherein the tetranucleotide AGAT repeats number present in the intronic polynucleotide of the gene GluR-5 on each different allele is obtained in step b) by determining the size of and/or sequencing the amplified products obtained after polymerase chain reaction.

6. A method according to claim 1, characterized in that said method further comprises assaying a biological sample from said subject for levels of at least an additional marker associated with the increased risk of developing said sporadic form of Alzheimer's disease, the presence of a significantly level of said at least one marker allowing to confirm if said subject is at increased risk of developing said sporadic form of Alzheimer's disease.

7. A method according to claim 6, characterized in that said second method comprises the following steps of:
   (i) detecting the presence or absence of an ApoE4 isoform in a biological sample of said subject by using at least one reagent that specifically detects apolipoprotein E type 4 (ApoE4), wherein said reagent is selected from the group consisting of antibodies that selectively bind ApoE4, and oligonucleotide probes that selectively bind to DNA encoding ApoE4; and
   (ii) observing if the presence of ApoE4 is or is not detected with said at least one reagent wherein the presence of ApoE4 confirms said subject is at increased risk of developing Alzheimer's disease.

8. A method according to claim 6, characterized in that said at least additional marker associated is selected from the group of markers consisting of bleomycin hydrolase gene polymorphism, FE65 protein gene polymorphism, polymorphic tetranucleotide ATTT repeat site within the intron 7 of the beta-amyloid precursor protein gene and the persyn (gamma-synuclein) gene polymorphism.

* * * * *